US010357154B2

(12) United States Patent
Kasthurirangan et al.

(10) Patent No.: US 10,357,154 B2
(45) Date of Patent: Jul. 23, 2019

(54) SYSTEMS AND METHODS FOR PROVIDING ASTIGMATISM CORRECTION

(71) Applicant: Abbott Medical Optics Inc., Santa Ana, CA (US)

(72) Inventors: Sanjeev Kasthurirangan, Fremont, CA (US); Stanley S. Bentow, Laguna Hills, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 699 days.

(21) Appl. No.: 14/472,737

(22) Filed: Aug. 29, 2014

(65) Prior Publication Data

US 2015/0062529 A1   Mar. 5, 2015

Related U.S. Application Data

(60) Provisional application No. 61/871,423, filed on Aug. 29, 2013.

(51) Int. Cl.
*A61B 3/107*  (2006.01)
*A61B 3/00*  (2006.01)

(52) U.S. Cl.
CPC .......... *A61B 3/107* (2013.01); *A61B 3/0025* (2013.01)

(58) Field of Classification Search
CPC .............................. A61B 3/107; A61B 3/0025

USPC ......................................................... 351/205
See application file for complete search history.

(56) References Cited

U.S. PATENT DOCUMENTS

2008/0004698 A1   1/2008  Das et al.
2013/0100403 A1   4/2013  Simpson

FOREIGN PATENT DOCUMENTS

WO   WO-2010054268 A2   5/2010
WO   WO-2012050622 A2   4/2012

OTHER PUBLICATIONS

Koch D.D., et al., "Contribution of Posterior Corneal Astigmatism to Total Corneal Astigmatism," Journal of Cataract & Refractive Surgery, 2012. vol. 38 (12), pp. 2080-2087.
Partial International Search Report for Application No. PCT/US2014/053382 dated Dec. 5, 2014, 7 pages.

*Primary Examiner* — Jack Dinh
(74) *Attorney, Agent, or Firm* — Johnson & Johnson Surgical Vision, Inc.

(57) ABSTRACT

A method of selecting a toric lens by taking into consideration the magnitude and orientation of the posterior cornea and/or the location of the incision axis is described. The magnitude and orientation of the posterior cornea can be calculated as a function of the measured pre-operative orientation of the steep meridian of the anterior cornea.

6 Claims, 6 Drawing Sheets

SYSTEMS AND METHODS FOR PROVIDING ASTIGMATISM CORRECTION

CROSS-REFERENCES TO RELATED APPLICATIONS

This application claims priority to U.S. Provisional Application No. 61/871,423 filed on Aug. 29, 2014, the entire contents of which are incorporated herein by reference.

BACKGROUND OF THE INVENTION

Field of the Invention

This application is directed at providing correction for astigmatism, including provision of systems and methods that use parameters that were previously not systematically accounted for to improve patient outcomes.

Description of the Related Art

Ophthalmic lenses, such as spectacles, contact lenses and intraocular lenses, may be configured to provide both spherical and cylinder power. The cylinder power of a lens is used to correct the rotational asymmetric aberration of astigmatism of the cornea or eye, since astigmatism cannot be corrected by adjusting the spherical power of the lens alone. Lenses that are configured to correct astigmatism are commonly referred to as toric lenses. As used herein, a toric lens is characterized by a base spherical power (which may be positive, negative, or zero) and a cylinder power that is added to the base spherical power of the lens for correcting astigmatism of the eye.

Toric lenses typically have at least one surface that can be described by an asymmetric toric shape having two different curvature values in two orthogonal axes, wherein the toric lens is characterized by a "low power meridian" with a constant power equal to the base spherical power and an orthogonal "high power meridian" with a constant power equal to the base spherical power plus the cylinder power of the lens. Intraocular lenses, which are used to replace or supplement the natural lens of an eye, may also be configured to have a cylinder power for reducing or correcting astigmatism of the cornea or eye.

Several pervasive problems arise in the selection of the proper toric lens configuration. These problems relate to the need to provide the correct lens configuration for the eye as it will exist after surgery. First, conventional selection is based on pre-operative anterior corneal keratometry. That is, the anterior surface of the cornea is measured before surgery to determine the curvature in orthogonal (e.g., horizontal and vertical) meridians and the toric lens configuration is selected primarily based upon this measurement. These measurements do not conventionally include measurements or estimates of the curvature of the posterior surface of the cornea, which can have a significant impact on a patient's overall astigmatism. Failure to account for the posterior corneal astigmatism can contribute to improper selection of toric lens configuration, which can require further correction.

Another problem arises from surgical steps taken after standard anterior corneal keratometry. That is, surgery can induce or exacerbate astigmatism. In practice, an incision is made at one location of the eye prior to introducing an intraocular lens into the eye. This incision changes the properties of the cornea. The changes can include steepening or flattening of the cornea along a meridian. If the incision flattens an already lower curvature meridian, the astigmatism also can be increased. Failure to accurately and systematically account for the contribution of this surgically induced astigmatism can lead to sub-optimal outcomes.

Astigmatism is sometime characterized as "against-the-rule" or "with-the-rule". FIG. 1 shows two meridians that may be found to have different curvatures in a cornea with astigmatism. The meridian A is a vertical meridian of the anterior surface of the cornea and the meridian B is a horizontal meridian of anterior surface of the cornea. If the curvature of vertical meridian A is steeper than that of horizontal meridian B, the eye is said to have "with-the-rule" astigmatism, as depicted in FIG. 1a. If the curvature of horizontal meridian B is steeper than that of vertical meridian A, the eye is said to have "against-the-rule" astigmatism, as depicted in FIG. 1b. While not always the case, typically the steep meridian of the anterior corneal surface tends to change from vertical to horizontal with increasing age, while that of the posterior corneal surface tends to retain its vertically steep alignment. Thus, posterior corneal astigmatism generally contributes to against-the-rule astigmatism. See, Douglas D. Koch et. al. "Contribution of posterior corneal astigmatism to total corneal astigmatism," J Cataract Refract Surg 2012; 38:2080-2087.

As discussed above, surgically induced astigmatism (SIA) can affect both the magnitude and direction of the principal astigmatic meridians of the cornea. Conventional methods include contribution from SIA based on an input diopter value provided by a physician at an incision location also provided by the physician. However, interactions between incision location and the orientation of the steep meridian in determining surgically induced astigmatism (SIA) are not known or conventionally part of toric IOL selection. Thus, although conventional methods do account for SIA, they do so in an un-controlled manner.

In view of the above discussed unknowns, surgeons have adopted a few "rules of thumb" when selecting an appropriate intraocular lens for implantation in a patient. For example, one rule of thumb is to over-correct against-the-rule astigmatism and to under-correct with-the rule astigmatism. Although, the rules of thumb may provide a satisfactory post-operative refractive outcome for some patients, many patients require additional correction (e.g., eyeglasses) after surgery due to the conventional inexact techniques. Even for the patients that have acceptable outcomes, the use of these rules of thumb complicates IOL selection for the physician. Accordingly, it would be desirable to have a method that can more precisely predict the post-surgical refractive outcome for most patients.

SUMMARY OF THE INVENTION

As discussed above, posterior corneal astigmatism can affect the post-operative refractive outcome, e.g., the need for spectacles, in patients undergoing eye surgery for correcting astigmatic defects. Furthermore, the location of the incision axis can also affect the post-operative refractive outcome. To improve post-operative refractive outcome, there exists a need to improve the accuracy of selection of a toric lens configured with easily obtained inputs. In some cases these algorithms and methods are configured to predict the magnitude and orientation of the curvature of the posterior cornea and/or the surgically induced astigmatism.

The embodiments disclosed herein include algorithms and methods to calculate the magnitude and orientation of posterior corneal astigmatism and the surgically induced astigmatism based on the steep axis of the anterior cornea. The algorithms and methods can be incorporated in a calculator that can provide a toric lens for implantation into a patient's eye. The algorithms and methods discussed herein can be implemented as instructions which can be executed by a computer processor to provide a toric lens for implantation in to a patient's eye.

A preferred embodiment includes a method of determining an optical power of a toric lens comprising: receiving a measurement related to an anterior corneal portion of an eye of a patient, wherein the measurement obtained by an ophthalmic diagnostic device; receiving information related to a position of an incision to be made in the eye of the patient for surgical purpose; and calculating an optical power of a toric lens based only on the received measurement and the received position, wherein the method is performed by a processor by executing instructions stored in a non-transitory computer medium. The receiving measurement related to an anterior corneal portion may include receiving orientation of the steep meridian of the anterior corneal portion. Calculating an optical power of a toric lens may include calculating a posterior corneal cylinder value due to posterior corneal astigmatism, the posterior corneal cylinder value determined by a function of a sine of the orientation of the steep meridian of the anterior corneal portion.

Another preferred embodiment includes a method of determining an optical power of a toric lens comprising: receiving a measurement related to an anterior corneal portion of an eye of a patient, the measurement obtained by an ophthalmic diagnostic device; receiving a measurement related to a posterior corneal portion of an eye of a patient, the measurement obtained by an ophthalmic diagnostic device; receiving information related to a position of an incision to be made in the eye of the patient for surgical purpose; and calculating an optical power of a toric lens based on the received measurement and the received position, wherein the method is performed by a processor by executing instructions stored in a non-transitory computer medium. The receiving measurement related to an anterior corneal portion may include receiving orientation of the steep meridian of the anterior corneal portion. Calculating an optical power of a toric lens may include calculating a value for surgically induced astigmatism, the surgically induced astigmatism value given by a function of a sine of the orientation of the steep meridian of the anterior corneal portion and a function of the position of the incision.

In another preferred embodiment, a method of determining an optical power of a toric lens to be surgically implanted in an eye of a patient by an incision made in the eye, the incision made along an incision axis, comprises: receiving a measurement related to pre-operative orientation of the steep meridian of the anterior cornea, the measurement obtained by an ophthalmic diagnostic device; obtaining a posterior corneal cylinder value indicative of the posterior corneal astigmatism; and calculating an optical power of a toric lens to be implanted in the eye of the patient based on the pre-operative steep meridian orientation and the posterior corneal cylinder value, wherein the method is performed by a processor by executing instructions stored in a non-transitory computer medium. Obtaining the posterior corneal cylinder value may include calculating the posterior corneal cylinder value from the orientation of the steep meridian of the anterior cornea. A further step may involve calculating a value for surgically induced astigmatism based on the orientation of the steep meridian of the anterior cornea. The surgically induced astigmatism value may be determined by a difference between the orientation of the steep meridian of the anterior cornea and an orientation of the incision axis. A further step may involve calculating a post-operative orientation of the steep meridian of the anterior cornea by adding the surgically induced astigmatism value to the pre-operative orientation of the steep meridian of the anterior cornea.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE PREFERRED EMBODIMENT

Figure 1:
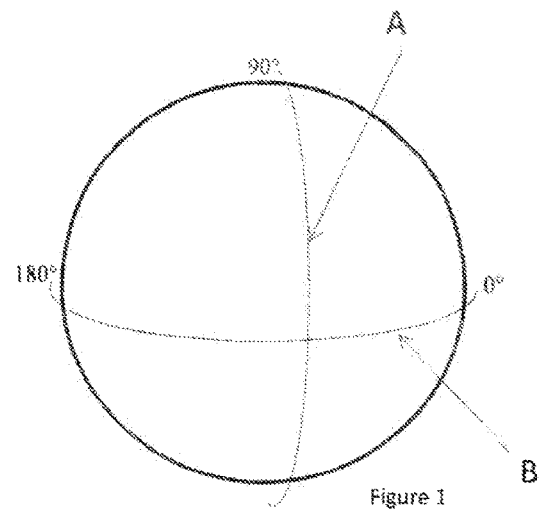
FIG. 1 is a schematic view of a cornea of the eye illustrating meridians that may have differing curvature resulting in astigmatism.
Figure 1A:
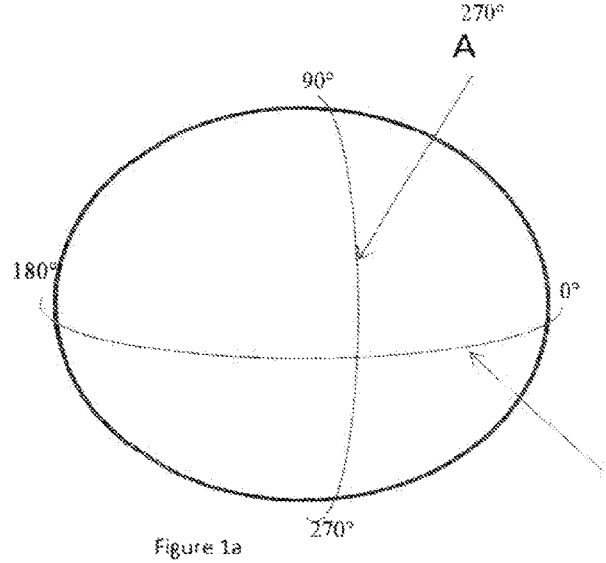
FIG. 1a illustrates a cornea having with-the-rule astigmatism.
Figure 1B:
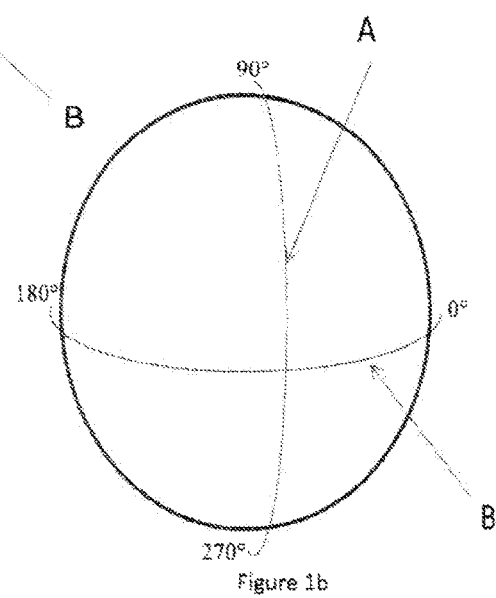
FIG. 1b illustrates a cornea having against-the-rule astigmatism.

Each and every feature described herein, and each and every combination of two or more of such features, is included within the scope of the present invention provided that the features included in such a combination are not mutually inconsistent.

Embodiments of the present invention are generally directed to toric lenses or surface shapes, and/or related methods and systems for fabrication and use thereof. Toric lenses according to embodiments of the present invention find particularly use in or on the eyes of human or animal subjects. Embodiments of the present invention are illustrated below with particular reference to intraocular lenses; however, other types of lenses fall within the scope of the present invention.

Embodiments of the present invention include prescribing, selecting and/or forming ophthalmic lenses and surfaces configured to reduce, or correct, astigmatism that are calculated by taking into consideration contribution of posterior corneal astigmatism. The contribution of posterior corneal astigmatism is in some embodiments, calculated by measuring the magnitude and orientation of anterior corneal astigmatism prior to surgically implanting the ophthalmic lenses and surfaces. Various embodiments also take into consideration, the effect of the location of the surgical incision axis on the overall astigmatism. Compared to conventional toric lens calculators, a calculator that includes contribution of the posterior corneal astigmatism and/or surgically induced astigmatism can provide patients with lower residual astigmatism following surgery, thus improving post-surgical refractive outcome.

As used herein, the term "optical power" means the ability of a lens or optic, or portion thereof, to converge or diverge light to provide a focus (real or virtual), and is commonly specified in units of reciprocal meters (m-1) or Diopters (D). When used in reference to an intraocular lens, the term "optical power" means the optical power of the intraocular lens when disposed within a media having a refractive index of 1.336 (generally considered to be the refractive index of the aqueous and vitreous humors of the human eye), unless otherwise specified. See ISO 11979-2, which is herein incorporated by reference in its entirety for all purposes as if fully set forth herein. Except where noted otherwise, the optical power of a lens or optic is from a reference plane associated with the lens or optic (e.g., a principal plane of an optic). As used herein, a cylinder power refers to the power required to correct for astigmatism resulting from imperfections of the cornea and/or surgically induced astigmatism.

As used herein, the terms "about" or "approximately", when used in reference to a Diopter value of an optical power, mean within plus or minus 0.25 Diopter of the referenced optical power(s). As used herein, the terms "about" or "approximately", when used in reference to a percentage (%), mean within plus or minus one percent (±1%). As used herein, the terms "about" or "approximately", when used in reference to a linear dimension (e.g., length, width, thickness, distance, etc.) mean within plus or minus one percent (1%) of the value of the referenced linear dimension.

As used herein, the term "post-operative refractive cylinder power" or the term "post-operative refractive cylinder outcome refers to the post-operative spherical and/or the cylinder power measured by an optometrist or an ophthalmic diagnostic device such as an autorefractor. As used herein, the term "pre-operative anterior corneal cylinder" refers to the cylinder power calculated from measurements associated with the pre-operative curvature and orientation of the anterior cornea that are obtained by an ophthalmic diagnostic device such as a keratometer or topographer. As used herein, the term "post-operative anterior corneal cylinder" refers to the cylinder power calculated from post-operative measurements associated with the curvature and orientation of the anterior cornea that are obtained by an ophthalmic diagnostic device such as a keratometer or topographer.

Artificial lenses (e.g., contact lenses or artificial intraocular lenses) can correct for certain visual impairments such as an inability of the natural lens to focus at near, intermediate or far distances; and/or astigmatism. Intraocular toric lenses have the potential for correcting astigmatism while also correcting for other vision impairments such as cataract, presbyopia, etc. However, in some patients implanted intraocular toric lenses may not adequately correct astigmatism and there may be a residual astigmatism that is substantially equal to or greater than the amount of astigmatism prior to implantation. In some patients, the implanted toric lenses can over-correct the astigmatism, while in some other patients, the implanted toric lenses can under-correct the astigmatism. This effect is illustrated in FIG. 2 discussed below.

Figure 2:
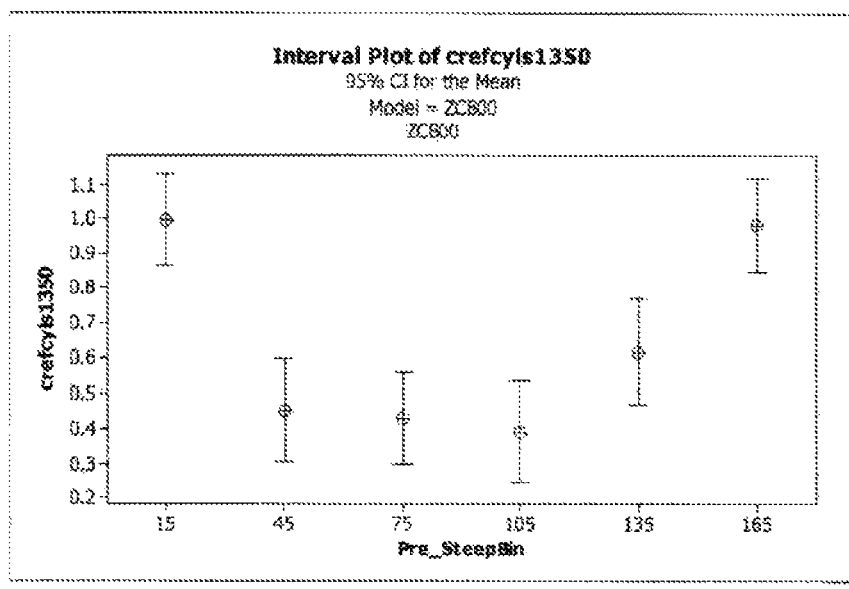
FIG. 2 illustrates an interval plot of the post-operative refractive cylinder power related to residual astigmatism for patients with different pre-operative orientations of the steep meridian of the anterior cornea who were implanted with a non-toric IOL.

FIG. 2 illustrates an interval plot of the post-operative refractive cylinder power related to residual astigmatism for different groups of patients with different pre-operative orientations of the steep meridian of the anterior cornea who were implanted with a particular implementation of a non-toric IOL. The different groups of patients had similar pre-operative cylinder powers, although they had different pre-operative orientations of the steep meridian of the anterior cornea. The measured post-operative refractive cylinder power can be resolved into a first orthogonal component represented by $J_0$ and a second orthogonal component represented by $J_{45}$.

It is observed from FIG. 2 that (i) patients having against-the-rule astigmatism, i.e., steep meridian of the anterior cornea oriented along approximately 0 degrees-30 degrees and 150 degrees-180 degrees had a post-operative refractive cylinder power of almost 1.0 D; and (ii) patients having with-the-rule astigmatism, i.e., steep meridian of the anterior cornea oriented along approximately 75 degrees-105 degrees had a post-operative refractive cylinder power less than or equal to about 0.5 D. Thus, patients having against-the-rule astigmatism had significant residual astigmatism after being implanted with a non-toric IOL while patients having with-the-rule astigmatism had much lower residual amounts of astigmatism after being implanted with a non-toric IOL. From the observations of FIG. 2, it can be concluded that the orientation of the steep meridian of the anterior cornea can affect the refractive outcomes in patients. Accordingly, refractive outcomes can be improved for patients by taking into account at least the orientation of the steep meridian of the anterior cornea.

It is desirable that the measured post-operative refractive cylinder power be as close to 0 as possible for most of the patients. However, in studies conducted on patients implanted with different implementations of toric lenses using conventional lens selection techniques, it was observed that a group of the patients having against-the-rule astigmatism, i.e., steep meridian of the anterior cornea oriented along approximately 0 degrees-30 degrees and approximately 150 degrees-180 degrees are under-corrected, i.e. the measured post-operative refractive cylinder is less than or equal to the measured pre-operative anterior corneal cylinder but is not 0. For example, a first orthogonal component ($J_{0\ XCREF}$) of the measured post-operative refractive cylinder power was about 0.5 D for patients having against-the-rule astigmatism and a first orthogonal component of the pre-operative anterior corneal cylinder power ($J_0$) of about +1.0 D. It was observed from the same study that a group of patients having with-the-rule astigmatism, i.e., steep meridian of the anterior cornea oriented along approximately 60 degrees-120 degrees are over-corrected, i.e. the post-operative refractive cylinder as measured shows that the post-operative cylinder has changed by an amount greater than the measured pre-operative anterior corneal cylinder and is not 0. For example, the first orthogonal component ($J_0$ $XCREF$) of the measured post-operative refractive cylinder power was about +0.5 D for patients having with-the-rule astigmatism and a first orthogonal component of the pre-operative anterior corneal cylinder power ($J_0$) of about −1.0 D.

One possible reason for the under-correction and over-correction for patients having different orientations of the steep meridian of the anterior cornea is that the contribution of the curvature of posterior cornea is not taken into consideration. Currently available toric lens calculators use (i) magnitude and orientation of the anterior corneal curvature, obtained by instruments such as a keratometer; (ii) the location of the surgical incision provided by a surgeon and (iii) an estimate of surgically induced astigmatism provided by the surgeon to prescribe an intraocular toric lens. However, the toric lens selection techniques currently commercially available do not take into consideration the curvature of the posterior cornea and/or the effect of surgically induced astigmatism on the location of the incision axis. As discussed above, it is now known that the magnitude and orientation of the curvature of the posterior cornea can affect the overall astigmatism and if not taken into account can degrade the post-surgical refractive outcome.

It is an object of the present disclosure to implement a toric lens calculator that also takes into consideration the curvature of the posterior cornea and/or the effect of the location of the surgical incision on the post-operative refractive cylinder. The curvature of the posterior cornea can be measured by sophisticated diagnostic methods such as Scheimpflug, Optical coherence tomography (OCT) or videokeratography. Alternately, the magnitude and orientation of the curvature of the posterior cornea can be calculated from the magnitude and orientation of the pre-operative anterior corneal curvature alone or in combination with other variables. Pre-operative anterior corneal curvature measurements can be obtained by using diagnostic methods such as keratometry, topography, etc.

Figure 3A:
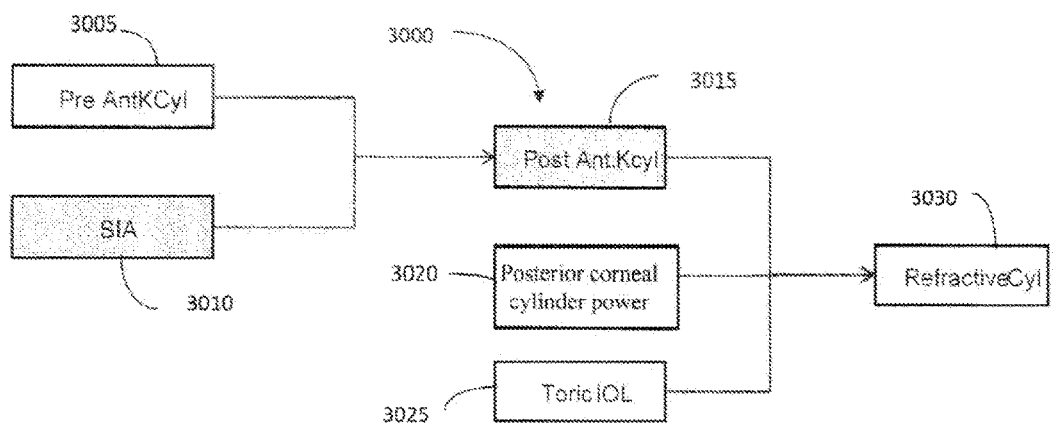
FIGS. 3a and 3b are flow charts illustrating different methods of calculating post-operative refractive outcome based on pre-operative anterior corneal curvature measurements.
Figure 3B:
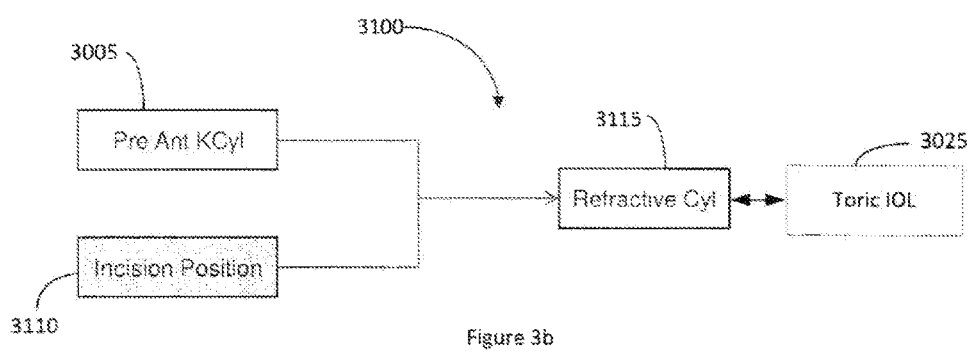

FIGS. 3a and 3b are flow charts illustrating different methods of calculating post-operative refractive outcome based on pre-operative anterior corneal curvature measurements. Having the ability to improve the prediction of the post-operative refractive outcome can be advantageous in selecting a toric IOL which when implanted can produce a desired post-operative refractive outcome.

FIG. 3a illustrates a flow chart 3000 that depicts a method of calculating the post-operative refractive cylinder from the measurements of the magnitude and orientation of the pre-operative anterior corneal curvature and the amount of surgically induced astigmatism provided by the surgeon. The method includes (i) receiving the measurements associated with anterior corneal curvature, as illustrated in block 3005; (ii) receiving or calculating the amount of surgically induced astigmatism (SIA) as illustrated in block 3010; (iii) calculating the post-operative cylindrical power of the anterior cornea, as illustrated in block 3015; (iv) receiving or predicting a posterior corneal cylinder value associated with the posterior corneal curvature, as illustrated in block 3020; (v) selecting a value for the toric IOL, as illustrated in block 3025 to produce a desired post-operative refractive outcome, e.g., cylinder power of 0 D or close to 0 D e.g., 0.5 D or less, as illustrated in block 3030.

The measurements associated with anterior corneal curvature can include the pre-operative anterior corneal cylinder power and the orientation of the steep meridian of the anterior cornea. In some implementations, the amount of surgically induced astigmatism can be a number between about 0.25 D and about 1.0 D that is provided by the surgeon based on the past experience and the location of the surgical incision.

The cylinder power as a result of SIA can be resolved into a first orthogonal component represented by $J_0SIA$ and a second orthogonal component represented by $J_{45}SIA$. In some implementations, the first and second orthogonal components of the cylinder power as a result of SIA can be calculated from a function of the pre-operative magnitude and orientation of the steep meridian of the anterior cornea. For example, a first orthogonal component $J_0SIA$ of the surgically induced astigmatism can be calculated from the equation $$J_0SIA = k_1 + k_2 \times \left(\left(\left(\sin(abs(\varphi)) * \frac{\pi}{180}\right)\right)\right) - 1,$$

wherein the variable $\varphi$ refers to the pre-operative orientation of the steep meridian of the anterior cornea or an angular difference between the pre-operative orientation of the steep meridian of the anterior cornea and the incision axis and $k_1$ and $k_2$ are constants. As used in this context, the "incision axis" can be an axis through the mid-point of the incision. In various implementations, $\varphi$ can have a value between 0 degrees and 180 degrees. In a specific implementation $k_1$ can have a value of 0.0082 and $k_2$ can have a value of 0.4239. As another example, a second orthogonal component $J_{45}SIA$ of the surgically induced astigmatism can be calculated from the equation $$J_{45}SIA = k_3 \times \left(0 - \left(\left(\cos(abs(\varphi)) * \frac{\pi}{180}\right)\right)\right),$$

wherein $k_3$ is a constant. In a specific implementation $k_3$ can have a value of 0.1499. In various implementations, the constants $k_1$, $k_2$ and $k_3$ can be determined using mathematical techniques such as recursion. The total surgically induced astigmatism can be calculated as a vector sum of the first orthogonal component $J_0SIA$ and the second orthogonal component $J_{45}SIA$. Although, in the implementation discussed herein, the first orthogonal component $J_0SIA$ and the second orthogonal component $J_{45}SIA$ are calculated using sine and cosine functions, in other implementations, they can be calculated using polynomial or other mathematical functions.

In some implementations, calculating the magnitude and orientation of the post-operative refractive cylinder power of the anterior cornea, as illustrated in block 3015 can include a summation of the pre-operative anterior corneal cylinder power and the surgically induced astigmatism that is either provided by the surgeon or calculated as discussed above. In other implementations, the post-operative anterior corneal cylinder power can be determined from an algebraic or a geometric function of the pre-operative anterior corneal cylinder power and the surgically induced astigmatism.

In some implementations, the cylinder power associated with the posterior corneal curvature can be obtained from the measurements associated with posterior corneal curvature. In some implementations, the posterior corneal cylinder power can be calculated from a function of the pre-operative orientation of the steep meridian of the anterior cornea. In some implementations, the posterior corneal cylinder power can be calculated from a function of the post-operative orientation of the steep meridian of the anterior cornea. For example, a first orthogonal component $J_0IntCyl$ of the posterior corneal cylinder power can be calculated from the equation $$J_0IntCyl = k_4 + k_5 \times \left(\left(\left(\sin(abs(\omega)) * \frac{\pi}{180}\right)\right)\right),$$

wherein the variable $\varphi$ refers to the post-operative orientation of the steep meridian of the anterior cornea and $k_4$ and $k_5$ are constants. As discussed above, in various implementations, φ can have a value between 0 degrees and 180 degrees. In a specific implementation $k_4$ can have a value of −0.2628 and $k_5$ can have a value of 1.00334. As another example, a second orthogonal component $J_{45}IntCyl$ of the posterior corneal cylinder power can be calculated from the equation $$J_{45}IntCyl = k_6 + k_7 \times \left(0 - \left(\left(\sin\left(\text{abs}(2*\omega)*\frac{\pi}{180}\right)\right)\right)\right),$$

wherein $k_6$ and $k_7$ are constants. In a specific implementation $k_6$ can have a value of −0.0119 and $k_7$ can have a value of 0.475. In various implementations, the constants $k_4$, $k_5$, $k_6$ and $k_7$ can be determined using mathematical techniques such as recursion. The total posterior corneal cylinder power can be calculated as a vector sum of the first orthogonal component $J_0IntCyl$ and the second orthogonal component $J_{45}IntCyl$. Although, in the implementation discussed herein, the first orthogonal component $J_0IntCyl$ and the second orthogonal component $J_{45}IntCyl$ are calculated using sine and cosine functions, in other implementations, they can be calculated using polynomial or other mathematical functions. In some embodiments, SIA can be ignored for the purpose of calculating the posterior corneal cylinder power, in which case, the post-operative orientation of the steep meridian of the anterior cornea ω is equivalent to the pre-operative orientation of the steep meridian of the anterior cornea φ.

FIG. 2 illustrates an interval plot of the post-operative refractive cylinder power related to residual astigmatism for patients with different pre-operative orientations of the steep meridian of the anterior cornea who were implanted with a non-toric IOL. As observed from FIG. 3a-1, patients having against-the-rule astigmatism (steep meridian of the cornea oriented at approximately 0 degrees and at approximately 180 degrees) had greater amount (approximately 1.0 D) of residual astigmatism following surgery as compared to patients having with-the-rule astigmatism who has less than 0.5D of residual astigmatism. This difference in the post-operative refractive cylinder power related to residual astigmatism could be attributed to the curvature of the posterior cornea or surgically induced astigmatism or both. It is also noted from FIG. 3a-1 that the post-operative refractive cylinder power has a sinusoidal dependence to the orientation of the pre-operative orientation of the steep meridian of the anterior cornea. Thus, it can be inferred that the curvature of the posterior cornea and/or surgically induced astigmatism can also have a sinusoidal dependence to the pre-operative orientation of the steep meridian of the anterior cornea In various embodiments, the functional relationship between the posterior corneal cylinder power and the pre-operative orientation of the steep meridian of the anterior cornea φ or post-operative steep meridian of the anterior cornea φ can be determined by (i) obtaining the difference between the measured pre-operative anterior corneal cylinder power and the post-operative refractive cylinder power of the anterior cornea for a number of patients in a population that was provided with a non-toric IOL; (ii) plotting the difference versus the pre-operative orientation of the steep meridian of the anterior cornea; and (iii) finding trigonometric or polynomial functions that best fit the difference data.

The functional relationship between SIA and the pre-operative orientation of the steep meridian of the anterior cornea φ or an angular difference between the pre-operative orientation of the steep meridian of the anterior cornea φ and the incision axis can be similarly determined.

A value for the toric IOL can be added to the received or calculated posterior corneal cylinder value and the calculated post-operative cylindrical power of the anterior cornea to obtain a desired post-operative refractive cylinder value. For example, in some implementations a toric IOL having a value that provides a post-operative refractive cylinder value of 0 D can be selected for implantation in a patient's eye.

FIG. 3b illustrates a flow chart 3100 that depicts a method of predicting the post-operative refractive cylinder power using the measurements of the pre-operative magnitude and orientation of the anterior corneal curvature and the location of the surgical incision as inputs. In various embodiments, other inputs such related to the measurement of the eye or the surgical method can be provided in addition to the pre-operative magnitude and orientation of the anterior corneal curvature and the location of the surgical incision. In one embodiment of the method 3100, the post-operative refractive cylinder power is predicted only from the input values of the pre-operative anterior corneal curvature and the location of the surgical incision. This method of calculation differs from the method 3000 in that the posterior corneal cylinder value is solely calculated from the orientation of the steep meridian of the anterior cornea and the location of the surgical axis, for example, by using the equations described above. If surgically induced astigmatism is taken into consideration, then it is solely calculated from the orientation of the steep meridian of the anterior cornea and the location of the surgical axis, for example, by using the equations described above. A value for the surgically induced astigmatism is not requested from the surgeon. The method includes (i) receiving the measurements associated with anterior corneal curvature, as illustrated in block 3005; (ii) receiving a location for the position of the incision axis, as illustrated in block 3110; (iii) calculating the post-operative refractive cylinder power, as illustrated in block 3115; and (iv) selecting a toric IOL that provides the desired post-operative refractive cylinder power.

Figure 4:
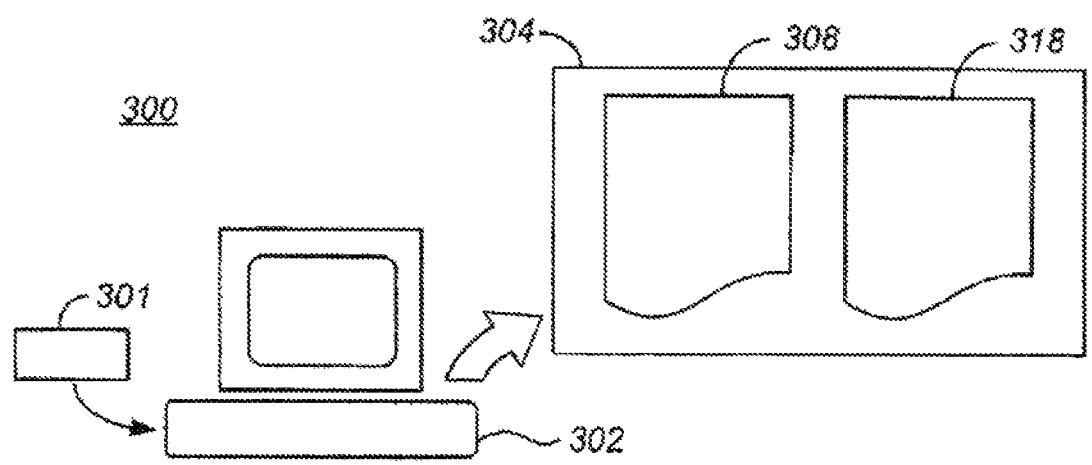
FIG. 4 is a block diagram that illustrates aspects of a system that can be used to implement the method described in FIGS. 3a and 3b.

The methods 3000 and 3100 can be implemented as a set of instructions which are stored in a non-transitory computer medium and executed by a computer processor. For example, the methods 3000 and 3100 can be implemented as a calculator that can be accessed over the internet. As another example, the methods 3000 and 3100 can be implemented as a mobile application which can be downloaded on a mobile device. As yet another example, the methods 3000 and 3100 can be implemented as a software program that is a part of an instrument. An instrument to implement the methods described herein can comprise a set of apparatuses, including a set of apparatuses from different manufacturers that are configured to perform the necessary measurements and calculations. Any instrument comprising all needed measurements (ocular and corneal measurements) as well as the needed calculations to implement the methods described herein, including but not limited to the methods 3000 and 3100 can be considered as an inventive embodiment. FIG. 4 is a block diagram illustrating an embodiment of a clinical system 300 that can be used to implement the methods described herein, including but not limited to the methods 3000 and 3100. The system 300 includes one or more apparatuses capable of performing the calculations, assessments and comparisons set forth in determining the magnitude and orientation of the curvature of the anterior and/or posterior cornea. The system 300 can include a diagnostic device 301, a processor 302, and a computer readable memory or medium 304 coupled to the processor 302. The computer readable memory 304 includes therein an array of ordered values 308 and sequences of instructions 318 which, when executed by the processor 302, cause the processor 302 to compute the surgically induced astigmatism and posterior corneal cylinder value discussed above.

The array of ordered values 308 can include one or more desired refractive outcomes, data obtained from measurements of the patient's eye, data related to one or more types of available IOL, parameters of refractive and diffractive features, etc. In some embodiments, the sequence of instructions 318 can include algorithms to perform calculations, customization, simulation, comparison, etc.

The processor 302 may be embodied in a general purpose desktop, laptop, tablet or mobile computer, and/or may comprise hardware and/or software associated with the device 301. In certain embodiments, the system 300 may be configured to be electronically coupled to another device, such as one or more instruments for obtaining measurements of an eye or a plurality of eyes and/or a laser surgical instrument. Alternatively, the system 300 may be adapted to be electronically and/or wirelessly coupled to one or more other devices.

Figure 5:
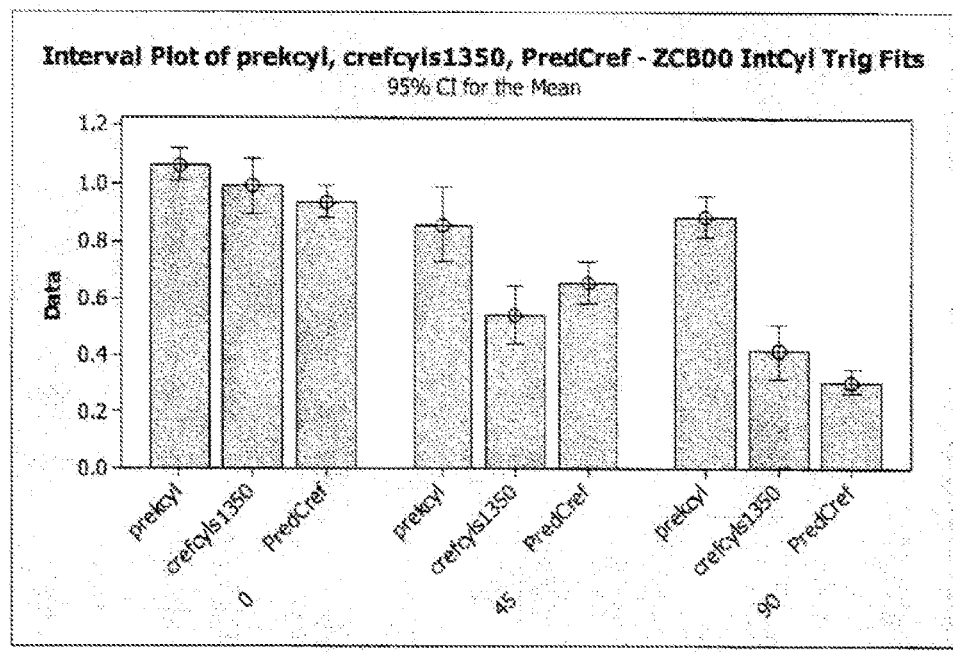
FIG. 5 is an interval plot that illustrates a comparison between measured post-operative refractive cylinder power when implanted with a non-toric IOL and the predicted post-operative refractive cylinder power for patients with different orientation of the steep meridian of the anterior cornea.

FIG. 5 is an interval plot that illustrates a comparison between measured post-operative refractive cylinder power when implanted with a non-toric IOL and the predicted post-operative refractive cylinder power for patients with different orientation of the steep meridian of the anterior cornea. The predicted post-operative refractive cylinder power was obtained by ignoring the contribution of SIA in the method 3000 and using the equations described above to calculate the first orthogonal component of the posterior corneal cylinder power $J_0IntCyl$ and the second orthogonal component of the posterior corneal cylinder power $J_{45}IntCyl$. It is observed from FIG. 5 that the predicted post-operative refractive cylinder power is approximately equal to the measured post-operative refractive cylinder power for patients having against-the-rule astigmatism as well as with-the-rule astigmatism. Thus, improved post-operative refractive outcomes can be achieved for patients having against-the-rule astigmatism as well as with-the-rule astigmatism by choosing an appropriate toric lens. In other words, both the under-correction in patients having against-the-rule astigmatism as well as the over-correction in patients having with-the-rule astigmatism can be reduced.

Figure 6:
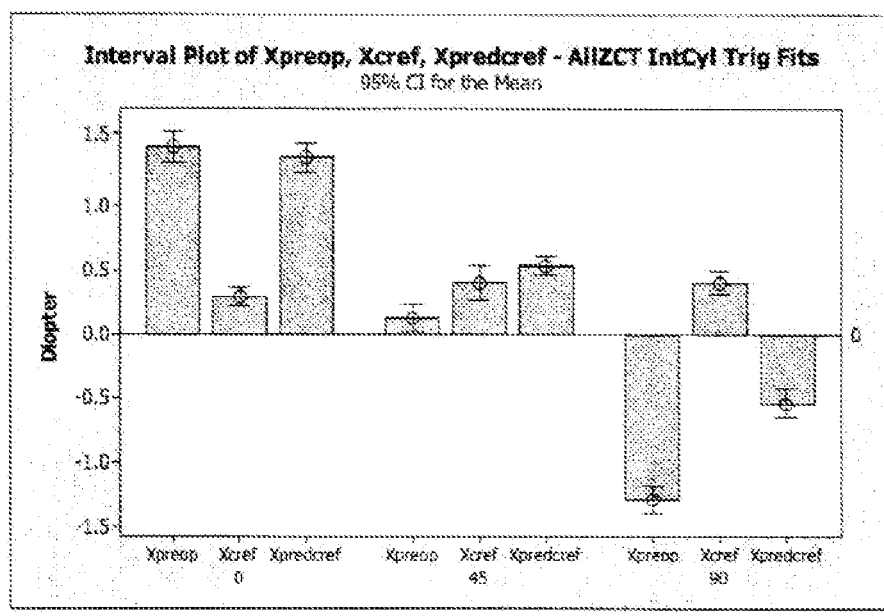
FIG. 6 is an interval plot illustrating the difference between the measured pre-operative anterior corneal cylinder power, the measured post-operative refractive cylinder power and the predicted post-operative refractive cylinder power for patients with different orientation of the steep meridian of the anterior cornea.

FIG. 6 is an interval plot illustrating the difference between the measured pre-operative anterior corneal cylinder power, the measured post-operative refractive cylinder power and the predicted post-operative refractive cylinder power for patients with different orientation of the steep meridian of the anterior cornea. The predicted post-operative refractive cylinder power is calculated using the methods 3000 and 3100 discussed above. In order to obtain the data for the plots of FIG. 6, a toric IOL was selected based on the predicted post-operative refractive cylinder power such that the post-operative refractive cylinder power was as close to 0 as possible. It is observed from FIG. 6 that when pre-operative anterior corneal cylinder power has positive value (e.g., against-the-rule astigmatism shown at bin '0'), the measured post-operative refractive cylinder power is slightly positive, which implies some negligible under-correction. When pre-operative anterior corneal cylinder power has positive value, the predicted post-operative refractive cylinder power without toric correction is also positive and is almost equal to the pre-operative anterior corneal cylinder power. By choosing an appropriate toric lens, the measured post-operative refractive cylinder can be almost 0 and the under-correction can be reduced.

It is further observed from FIG. 6 that for "with-the-rule" patients (e.g., for bin '90') when pre-operative anterior corneal cylinder power has a negative value, the post-operative refractive cylinder power is positive which implies over-correction. It is further observed from FIG. 6 that a reduction in the post-operative cylinder is predicted even without toric correction for patients having with-the-rule astigmatism. That is, the Xpredcref value predicts that without toric correction, the post-operative refractive cylinder power for these patients will be on average about −0.5 diopters. Thus, a lens selection device or method as discussed herein can be used to identify a lens that reduces over-correction for these patients. For instance, when pre-operative anterior corneal cylinder power for these patients has a value of about −1.3 diopters, a toric lens selected by the apparatuses or methods herein can be one that provides post-operative refractive cylinder power that is positive but that has a relatively low magnitude, e.g., within about 0.5 diopters of 0. Thus, it can be concluded that by taking the magnitude and curvature of the posterior cornea into consideration, over-correction for patients having with-the-rule astigmatism and under-correction for patients having against-the-rule astigmatism can be reduced.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A method of determining an optical power of a toric lens, the method comprising:
   receiving a measurement related to an anterior corneal portion of an eye of a patient, the measurement obtained by an ophthalmic diagnostic device;
   receiving information related to a position of an incision to be made in the eye of the patient for surgical purpose; and
   calculating the optical power of the toric lens based only on the received measurement and the received position, wherein the method is performed by a processor configured to execute instructions stored in a non-transitory computer medium which, when executed by the processor, cause the processor to calculate the optical power of the toric lens.

2. The method of claim 1, wherein receiving the measurement related to the anterior corneal portion includes receiving an orientation of the steep meridian of the anterior corneal portion.

3. The method of claim 2, wherein the calculating the optical power of the toric lens includes calculating a posterior corneal cylinder value due to posterior corneal astigmatism, the posterior corneal cylinder value determined by a function of a sine of the orientation of the steep meridian of the anterior corneal portion.

4. A method of determining an optical power of a toric lens, the method comprising:
   receiving a measurement related to an anterior corneal portion of an eye of a patient, the measurement obtained by an ophthalmic diagnostic device;
   receiving a measurement related to a posterior corneal portion of an eye of a patient, the measurement obtained by an ophthalmic diagnostic device;
   receiving information related to a position of an incision to be made in the eye of the patient for surgical purpose; and
   calculating the optical power of the toric lens based on the received measurement and the received position,
   wherein the method is performed by a processor configured to execute instructions stored in a non-transitory computer medium which, when executed by the processor, cause the processor to calculate the optical power of the toric lens.

5. The method of claim 4, wherein receiving the measurement related to the anterior corneal portion includes receiving an orientation of the steep meridian of the anterior corneal portion.

6. The method of claim 4, wherein the calculating the optical power of the toric lens includes calculating a value for surgically induced astigmatism, the surgically induced astigmatism value given by a function of a sine of the orientation of the steep meridian of the anterior corneal portion and a function of the position of the incision.

* * * * *